US011278645B2

(12) United States Patent
Luyten et al.

(10) Patent No.: US 11,278,645 B2
(45) Date of Patent: Mar. 22, 2022

(54) ENGINEERING FUNCTIONAL BONE ORGANS (71) Applicant: KATHOLIEKE UNIVERSITEIT LEUVEN, Leuven (BE)

(72) Inventors: Frank Luyten, Kraainem (BE); Luis Freitas Mendes, Heverlee (BE); Gabriella Nilsson Hall, Leuven (BE); Ioannis Papantoniou, Brussels (BE); Liesbet Geris, Eliksem (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 315 days.

(21) Appl. No.: 16/617,130

(22) PCT Filed: May 30, 2018

(86) PCT No.: PCT/EP2018/064254
§ 371 (c)(1),
(2) Date: Nov. 26, 2019

(87) PCT Pub. No.: WO2018/220051
PCT Pub. Date: Dec. 6, 2018

(65) Prior Publication Data
US 2021/0146008 A1 May 20, 2021

(30) Foreign Application Priority Data

May 30, 2017 (GB) ..................................... 1708590
Aug. 4, 2017 (LU) ................................... LU100361

(51) Int. Cl.
A61L 27/38 (2006.01)
C12N 5/077 (2010.01)

(52) U.S. Cl.
CPC ....... A61L 27/3821 (2013.01); A61L 27/3817 (2013.01); A61L 27/3895 (2013.01); C12N 5/0655 (2013.01); A61L 2300/64 (2013.01); A61L 2430/02 (2013.01); C12N 2500/32 (2013.01); C12N 2500/38 (2013.01); C12N 2501/04 (2013.01); C12N 2501/115 (2013.01); C12N 2501/15 (2013.01); C12N 2501/155 (2013.01); C12N 2501/19 (2013.01); C12N 2501/33 (2013.01); C12N 2501/727 (2013.01); C12N 2506/13 (2013.01)

(58) Field of Classification Search
None
See application file for complete search history.

(56) References Cited

U.S. PATENT DOCUMENTS 7,887,843 B2 * 2/2011 Libera .................. C12N 5/0654
424/489

OTHER PUBLICATIONS

Nilsson-Hall et al, Advanced Science, 2020, 7, 1902295. (Year: 2020).*
J. Lei j ten et al: "Bioinspired seeding of biomaterials using three dimensional microtissues induces chondrogenic stem cell differentiation and cartilage formation under growth factor free conditions," Sci Rep., Nov. 3, 2016 (Nov. 3, 2016), p. 36011, XP055416750.
Johanna Bolander et al: "Healing of a Large Long-Bone Defect through Serum-Free In Vitro Priming of Human Periosteum-Derived Cells," Stem Cell Reports, vol. 8, No. 3, Feb. 9, 2017 (Feb. 9, 2017), pp. 758-772, XP055416794.
Hanada K et al: "BMP-2 Induction and TGF-Betai Modulation of Rat Periosteal Cell Chondrogenesis," Journal of Cellular Biochemi, Wiley-Liss Inc, US, vol. 81, No. 2, Jan. 1, 2001 (Jan. 1, 2001), pp. 284-294, XP008021250.
Luis Filipe Mendes et al: "Combinatorial Analysis of Growth Factors Reveals the Contribution of Bone Morphogenetic Proteins to Chondrogenic Differentiation of Human Periosteal Cells," Tissue Engineering. Part C, Methods Dec. 2008, vol. 22, No. 5, May 1, 2016 (May 1, 2016), pp. 473-486, XP055416724.
M. Lehmann et al: "Three-dimensional scaffold-free fusion culture: the way to enhance chondrogenesis of in vitro propagated human articular chondrocytes," European Journal of Histochemistry: EJH, vol. 57, No. 4, Jan. 1, 2013 (Jan. 1, 2013), pp. 31-31, XP055417117.
Atala et. al., "Engineering Complex Tissues," Science Translation Medicine, vol. 4, Issue 160, Nov. 14, 2012, pp. 1-11, Washington, DC.
Bahney et. al., "Stem Cell-Derived Endochondral Cartilage Stimulates Bone Healing by Tissue Transformation," Journal of Bone and Mineral Research, vol. 29, No. 5, May 2014, pp. 1269-1282.
Jukes, et al., "Endochondral bone tissue engineering using embryonic stem cells", PNAS, vol. 105, No. 19, pp. 6840-6845, May 13, 2008.
Holm et. al., "Loss of bone sialoprotein leads to impaired endochondral bone development and mineralization," Bone 71 (2015), pp. 145-154.
Lenas, et al., "Developmental Engineering: A new Paradigm for the Design and Manufacturing of Cell-Based Products. Part I: From Three-Dimensional Cell Growth to Biomimetics of In Vito Development", Tissue Engineering, vol. 15, No. 4, pp. 381-394, Nov. 4, 2009.
Lenas, et al., "Developmental Engineering: A new paradigm for the Design and Manufacturing of Cell-based products. Part II: From Genes to Networks: Tissue engineering from the Viewpoint of Systems Biology and Network Science", Tissue Engineering, vol. 15, No. 4, pp. 395-422, Nov. 4, 2009.
Li, et al., "The Effect of Oxygen Tension on Human Articular Chondrocyte Matrix Synthesis: Integration of Experimental and Computational Approaches", Biotechnology and Bioengineering, vol. 111, No. 9, pp. 1876-1885, Sep. 2014.
Lipsitz, et al., "Quality cell therapy manufacturing by design", Nature Biotechnology, Perspective, vol. 34, No. 4, pp. 393-400, Apr. 2016.

(Continued)

Primary Examiner — Allison M Fox
(74) Attorney, Agent, or Firm — Dinsmore & Shohl LLP (57) ABSTRACT The present invention describes in vitro methods for producing a cellular composition with in vivo bone forming potential.

20 Claims, 8 Drawing Sheets (56) References Cited

OTHER PUBLICATIONS

Mackie, et al., "The skeleton: a multi-functional complex organ. The growth plate chondrocyte and endochondral ossification". Thematic Review, Journal of Endocrinology, pp. 109-121, 2011.
Teixeira, et al., "High Throughput Generated Micro-Aggregates of Chondrocytes Stimulate Cartilage formation In Vitro and In Vivo", European Cells and Materials, vol. 23, pp. 387-399, 2012.
Nakao, et al., "The development of a bioengineered organ germ method", Nature Methods, vol. 4, No. 3, pp. 227-230, Mar. 2007.
Scotti, et al., "Recapitulation of endochondral bone information using human adult mesenchymal stem cells as a paradigm for developmental engineering", PNAS, vol. 107, No. 16, pp. 7251-7256, Apr. 20, 2010.
Scotti, et al., "Engineering of a functional bone organ through endochondral ossification", PNAS, vol. 110, No. 10, pp. 3997-4002, Mar. 5, 2013.
Van Gastel, et al., "Expansion of Murine Periosteal Progenitor Cells with Fibroblast Growth Factor 2 Reveals an Intrinsic Endochondral Ossification Program Mediated by Bone Morphogenetic Protein 2", Stem Cells, Regenerative Medicine, pp. 2407-2418, 2014.
Roberts, et al., "The combines bone forming capacity of human periosteal derived cells and calcium phosphates", Elsevier, Biomaterials, pp. 4393-4405, 2011.
International Search Report in reference to co-pending European Patent Application No. PCT/EP2018/064254 dated May 30, 2018.

\* cited by examiner

Figure 1

B - chondrogenic markers

ENGINEERING FUNCTIONAL BONE ORGANS

FIELD OF THE INVENTION

The present invention relates to cell based methods for making cellular compositions that allow healing of bone, disorders. The application further provides pharmaceutical compositions comprising said cellular compositions and method of treatments using said cellular compositions. The application further relates to said cellular compositions made by said methods and to their use in the treatment of bone disorders. The current invention further relates to method of treatments of bone disorders.

BACKGROUND

The inability to control complexity in 3D cell culture formats for cartilage and bone fracture healing has to date hampered the translation of laboratory-scale observations to a clinical and industrial setting where robust clinical outcomes must be guaranteed [Atala et al. (2012) *Sci Transl Med* 4, 160rv112]. The lack of a manufacturing strategy where measurable quality attribute indicators, of either cells or tissue units, can provide information on their potency constitutes currently a major bottleneck for incorporating design principles in living implant manufacturing [Lipsitz et al. (2016) *Nat Biotechnol* 34, 393-400]. For instance, a major limitation in using scaffold-free culture methods for inducing chondrogenic differentiation is the initial size of the in vitro "manufactured" tissue. Current protocols use high numbers of cells in order to obtain the initial condensation usually in the range of $10^5$ to $5\times10^5$ cells. This imposes adverse diffusion dominated environments leading in one hand to uncontrolled differentiation events (in terms of spatial and temporal patterns) while at extreme cases results in cell death [Li. et al. (2014) *Biotechnol. Bioeng.* 111, 1876-1885]. The generation of functional tissues from progenitor cells is poised to revolutionize regenerative medicine, by providing biological substitutes for lost or damaged tissues due to injury, disease, or aging [Nakao et al. (2007) *Nat Methods* 4, 227-230]. Increasing understanding of embryonic development and stem cell biology has greatly influenced tissue engineering regarding the choice of cell types, regulation of stem cell differentiation and tissue formation, by providing spatially and temporally regulated biochemical and physical cues. The concept that using stem cells and progenitor cells to obtain bone by recapitulating biologic processes encountered in embryonic long bone development, via endochondral ossification, constituted a paradigm shift in bone tissue engineering termed as "developmental engineering" [Lenas et al. (2009) *Tissue Eng Part B-Re* 15, 381-394; Lenas et al. (2009) *Tissue Eng Part B-Re* 15, 395-422 (2009)]. Investigations inspired by this strategy showed that by using embryonic or mesenchymal stromal cells (MSCs) one could recapitulate endochondral ossification in ectopic environments while this was also demonstrated for MSCs in orthotopic implantation sites [Jukes et al. *Proc. Natl. Acad. Sci. USA* 105, 6840-6845 (2008); Scotti et al. (2010) *Proc. Natl. Acad. Sci. USA* 107, 7251-7256; Scotti et al. (2013) *Proc. Natl. Acad. Sci. USA* 110, 3997-4002; Bahney et al. (2014) *J. Bone Min. Res.* 29, 1269-1282].

A major limitation of the aforementioned studies was however the lack of evidence for the semi-autonomy of the engineered "whole-tissue" therefore lack of demonstration of their potency in forming a whole-organ structure upon implantation. Desired biological events (in vivo) were only observed in fragments of the implanted tissue while a large part still contained "contaminating" tissues posing major concerns for regulatory body approval. Accordingly, there remains a need for better methods to treat bone, disorders. Moreira Teixeira et al. (2012) *Eur Cell Mater.* 23, 387-399, discloses methods and media to generate microaggregate cultures with glycosaminoglycan expressingtissue forming potential when encapsulated in hydrogel.

Mendes et al. (2016) *Tissue Eng Part C Methods.* 22(5), 473-486, discloses media to generate micromass cultures with cartilage forming potential. Cells which have been induced to mineralisation fail to form bone or cartilage.

Bolander et al. (2017) *Stem Cell Reports.* 8(3), 758-772, discloses methods and media to generate microaggregate cultures with bone forming potential in combination with hydrogel carrier.

SUMMARY

The present invention provides a novel approach for healing critical size bone defects through the use of a microtissue cellular composition derived from human periosteal cells. These compositions of typically a few hundred cells have a cartilage intermediate phenotype, and are able to undergo endochondral ossification, upon subcutaneous ectopic implantation, resulting in bone-like structures. They contain bone tissue, TRAP positive cells, CD31 positive cells as well as a bone marrow compartment at their center. In addition, this property was maintained across tissue scale. The microtissues are able to fuse into larger structures via self-assembly (fused microtissues). Once implanted these larger tissue structures result in the formation of de novo mature bone tissue. It should be noted that all cases exhibited lack fibrotic (contaminating) tissue. The implants are able to regenerate critical size defects in nude mice when implanted orthotopically, possessing a significant bone marrow compartment.

Surprisingly the fused microtissues retain the ability to form bone tissue. Furthermore, markers for high quality bone formation are more prominent in bone tissue obtained from fused microtissues than in bone tissue obtained from a plurality of individual microtissues in hydrogel carrier.

The fused microtissues have the advantage that they can heal a critical size bone defect faster and with higher presence of donor cells than with a carrier wherein a plurality of individual microtissues is present.

The assembly of multiple pre-hypertrophic microtissues by fusion into a larger aggregates provides an easy-to-handle scaffold-free implant resulting in full bridging of a critically sized long bone defect by the formation of cortical-like bone tissue, containing bone marrow with the absence of fibrous tissue.

The present disclosure relates to the creation of a cell based implant for treatment of bone disorders. Micro aggregates are formed from progenitor cells and matured into cartilage intermediate micro tissues exhibiting pre-hypertrophic phenotype. Maturation is promoted by culture in a serum free media containing at least one BMP resulting in micro tissues with pre-hypertrophic phenotype generating their capacity to form bone upon implantation. Said micro tissues can/are subsequently fused to generate larger fused microtissues suitable for the site of implantation, e.g. bone, cartilage or joint defects.

Numbered statements of disclosures herein are:

1. An in vitro method for producing a cellular composition with in vivo bone forming potential, the method comprising the steps of:
   generating micro-aggregates of between 25 and 50.000 periosteum derived cells;
   culturing said micro-aggregates in a serum free medium, comprising at least one BMP, in order to allow said micro aggregates to differentiate into a microtissue with a pre-hypertrophic cartilage phenotype;
   fusing, in the absence of a scaffold, at least 300 of said micro-tisssue into a fused microtissue.

2. The method according to statement 1, wherein micro-aggregates are cultured in said serum-free medium for a period from between 3 and 56 days.

3. The method according to statement 1 or 2, comprising the step of further culturing the fused microtissue.

4. The method according to any one of statement 1 to 3, further comprising the step of formulating said fused microtissue into a biocompatible carrier.

5. The method according to statement 4, wherein said biocompatible carrier comprises collagen, fibrinogen, calcium phosphate, carboxy methyl cellulose, polyglycolic acid (PGA), Poly-lactic acid (PLA), poly-caprolactone (PCL), graphene, hydrogel or a combinations thereof.

6. The method according to any one of statements 1 to 5, wherein said micro-aggregates contain about 25 to 5000 cells per generated aggregate.

7. The method according to any one of statements 1 to 6, wherein said micro-aggregates contain about 250 cells per generated aggregate.

8. The method according to any one of statements 1 to 7, wherein about 300 to 3000, to 25.000, to 250.000, to 1.000.000 or even up to 20.000.000 microtissues are fused into a fused microtissue.

9. The method according to any one of statements 1 to 8, wherein about 6000 microtissues are fused into a fused microtissue.

10. The method according to any one of statements 1 to 9, wherein the at least one BMP is selected from the group consisting of BMP2, BMP4, BMP6, BMP7, BMP9, and any combination thereof.

11. The method according to any one of statements 1 to 10, wherein the at least one BMP is BMP2, BMP6 or a combination of BMP-2 and BMP-6.

12. The method according to any of the statements 1 to 11, wherein the concentration of the at least one BMP is between about 0.1 to 1000 ng/ml.

13. The method according to any one of statements 1 to 12, wherein the at least one BMP is a combination of BMP-2 and BMP-6.

14. The method according to statement 13, wherein the concentration of BMP-2 is between about 10 to 1000 ng/ml and the concentration of BMP-6 is between about 0.1 to 10 ng/ml.

15. The method according to statement 13, wherein the concentration of BMP-2 is about 100 ng/ml and the concentration of BMP-6 is about 1 ng/ml.

16. The method according to any of the statements 1 to 15, wherein said medium further comprises at least one growth factor selected from the group consisting of TGFbeta1, FGF2, GDF5 and any combination thereof.

17. The method according to statement 16, wherein the concentration of said at least one growth factor in the medium is from about 0.01 ng/ml to about 1000 ng/ml.

18. The method according to statement 16, wherein the concentration of said at least one growth factor in the medium is from about 0.01 ng/ml to about 100 ng/ml, and more specifically the concentration of TGFbeta1 is about 10 ng/ml, the concentration of FGF2 is about 0.2 ng/ml, and the concentration of GDF5 is about 100 ng/ml.

19. The method according to any one of statements 1 to 18, wherein the medium comprises: about 10 ng/ml TGF-beta1, about 0.2 ng/ml FGF2, about 100 ng/ml GDF5, about 100 ng/ml BMP2, and about 1 ng/ml BMP6.

20. The method according to any one of statements 1 to 19, wherein the medium comprises: 1 to 100 ng/ml TGF beta 1, 0.05 to 10 ng/ml FGF2, 1 to 250 ng/ml BMP2, 0.25 to 2.5 ng/ml BMP6 and 1 to 250 ng/ml GDF5.

21. The method according to any of statements 1 to 20, wherein said medium further comprises Dexamethasone, a Rho-kinase inhibitor and Ascorbic Acid.

22. The method according to statement 21, wherein said medium comprises: about 10 to 1000 µM Dexamethasone, about 2 µM to about 200 µM Rho-kinase inhibitor, and about 10 to 1000 µM Ascorbic Acid.

23. The method according to statement 21 or 22, wherein said medium comprises about 100 nM Dexamethasone, about 20 µM Rho-kinase inhibitor, and about 100 µM Ascorbic Acid.

24. The method according to any one of the statements 22 to 24, wherein said Rho-kinase inhibitor is Y27632.

25. The method according to any one of statements 1 to 24, wherein the serum free medium comprises: a basal cell culture medium, antibiotic-antimycotic, proline, insulin, transferrin, selenious acid, bovine serum albumin, linoleic acid.

26. A cellular composition obtained by the method according to any one of statements 1 to 25, for use in the treatment of a bone disorder.

27. The cellular composition according to statement 26, for use in accordance with statement 26, wherein said bone, cartilage or joint disorder is a bone fracture, a non-healing bone defect, an osteochondral defect or damaged joint surface, or a metabolic bone disease.

28. A method of treatment of a bone, cartilage or joint disorder in an animal, comprising the administration of a cellular composition obtained by the method according to any one of statements 1 to 25.

The invention is summarized as follows

A first aspect of the invention relates to in vitro methods for producing a cellular composition with in vivo bone forming potential, the method comprising the steps of:
   generating micro-aggregates of between 25 and 50.000 periosteum derived cells;
   culturing said micro-aggregates for at least 10 days in a serum free medium, comprising BMP2, in order to allow said micro aggregates to differentiate into a microtissue with a pre-hypertrophic cartilage phenotype;
   fusing, in the absence of a scaffold, at least 300 of said micro-tissues into a fused microtissue.

In embodiments hereof the micro-aggregates are cultured for at least 12 days, at least 14 days, at least 21 days, between 10 to 28 days, between 14 to 28 days, between 14 to 21 days, 21 to 28 days in said serum free medium comprising BMP2.

In embodiments of these methods the concentration of BMP2 is between 50 and 150 ng/ml, between 75 and 125 ng/ml or about 100 ng/ml BMP2.

In embodiments thereof said microtissue with pre-hypertropic cartilage phenotype expresses one or more hypertrophic related markers such as ColX, IHH, ALP, or a mineralization related marker such as BSP. Compared to aggregates prior to the cultivation in the serum free medium, the microtissues typically express more than a 100 fold, a 500 fold or a 1000 fold expression of CoIX. Compared to aggregates prior to the cultivation in the serum free medium, the microtissues typically express more than a 2 fold, more than a 5 fold, more than a 10 fold, or more than a 20 fold expression of IHH. Compared to aggregates prior to the cultivation in the serum free medium, the microtissues typically express more than a 5 fold, more than a 10 fold, more than a 20 fold expression of ALP. Compared to aggregates prior to the cultivation in the serum free medium, the microtissues typically express more than a 5 fold, more than a 10 fold, more than a 100 fold, more than a 1000 fold or more than a 5000 fold expression of BSP.

In embodiments of these methods, free from FGF2 or comprises between 0.05, 0.1 to 0.5, 1, 5 or 10 ng/FGF2.

In embodiments of these methods micro-aggregates are generated of between 25, 50, 100, 200, 500, up to 1000, 2000, 5.000 periosteum derived cells. Ranges encompassing any of the above lower and upper limits are envisaged In embodiments of these methods micro-aggregates are generated of between 100 and 500 cells or of about 250 periosteum derived cells.

Embodiments of these methods comprising the step of further culturing the fused microtissue. Typically the fused microtissue is formed after 24 hours. This fused microtissue can be used as such for implantation or can be cultivated further, for example for an additional 2, 5, 7, or 14 days Embodiments of these methods comprise the step of formulating said fused microtissue into a biocompatible carrier. A non-limiting list hereof comprises omprises collagen, fibrinogen, calcium phosphate, carboxy methyl cellulose, polyglycolic acid (PGA), Poly-lactic acid (PLA), poly-caprolactone (PCL), graphene, hydrogel or a combinations thereof. In embodiments of these methods, about 300 to $20\times10^6$ microtissues are fused into a fused microtissue. The number of microtissues to be used depends from the initial size of the aggregates and the size of the bone defect.

In embodiments of these methods, about 6000 microtissues are fused into a fused microtissue.

In a particular embodiment, the serum free medium comprises about 10 ng/ml TGFbeta1, about 0.2 ng/ml FGF2, about 100 ng/ml GDF5, about 100 ng/ml BMP2, and about 1 ng/ml BMP6.

In a particular embodiment, the serum free medium comprises 1 to 100 ng/ml TGF beta 1, 0.05 to 10 ng/ml FGF2, 1 to 250 ng/ml BMP2, 0.25 to 2.5 ng/ml BMP6, 1 to 250 ng/ml GDF5.

In a particular embodiment, the serum free medium comprises comprises Dexamethasone, a Rho-kinase inhibitor such as Y27632; and Ascorbic Acid, for example about 10 to 1000 nM Dexamethasone, about 2 μM to about 200 μM Rho-kinase inhibitor, and about 10 to 1000 μM Ascorbic Acid, or about 100 nM Dexamethasone, about 20 μM Rho-kinase inhibitor, and about 100 μM Ascorbic Acid.

In embodiments of these methods the serum free medium comprises, basal cell culture medium, anantibiotic-antimycotic proline, insulin, transferrin, selenious acid, bovine serum albumin and linoleic acid.

A second aspect of the invention relates to cellular compositions obtained by the methods of the first object for use in the treatment of a bone disorder, such as a bone fracture, a non-healing bone defect, an osteochondral defect, or a metabolic bone disease.

A third aspect of the invention relates to methods of treatment of a bone disorder in an animal, comprising the administration of a cellular composition obtained by the methods of the first aspect.

BRIEF DESCRIPTION OF DRAWINGS

FIG. 1. Long-term culture into fused microtissues follows early patterns of endochondral ossification. (a) Schematic overview of the process starting with cell aggregation, condensation and differentiation followed by microtissues fusion and implantation in ectopic and orthotopic environment. (b) Representative bright-field images of μ-aggregates over time. (c) DNA quantification over time. The DNA is normalized to Day 0. (d) Semi-quantification of cell proliferation in μ-aggregates over time. EdU fluorescent area is normalized to DAPI fluorescent area.

FIG. 5. Healing of critical sized long bone defect in mouse. (a) Schematic visualization of implant formation. (b) Bright field image 1 h after microtissue seeding. (c) Photograph of a 5 mm tibia defect after healing. (d) X-ray images of tibia defect after 3 w microtissue construct implantation. (e) Negative control: X-ray of empty after 8 weeks. (f) 3D rendering of nanoCT images of defect 3 w microtissue construct over time. (g) Cross section of 3D rendering of tibia defect 8 weeks after implantation.

DETAILED DESCRIPTION

The present invention will be described with respect to particular embodiments but the invention is not limited thereto only by the claims. Any reference signs in the claims shall not be construed as limiting the scope thereof.

Definitions

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. As an example, in case the term about is used in combination with a certain amount of days, it includes said specific amount of days plus or minus 1 day, eg. about 6 days include any amount of days between 5 and 7. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The term "animal", "patient" or "subject" is used herein to describe an animal, especially including a domesticated mammal and preferably a human, to whom a treatment or procedure is performed. For treatment of those conditions or disease states which are specific for a specific animal such as a human patient, the term patient refers to that specific animal. In most instances, the patient or subject of the present invention is a domesticated/agricultural animal or human patient of either gender.

As used herein, the terms "treat" or "treatment" refer to both therapeutic treatment and prophylactic or preventative measures. Beneficial or desired clinical results include, but are not limited to, prevention of an undesired clinical state or disorder, reducing the incidence of a disorder, alleviation of symptoms associated with a disorder, diminishment of extent of a disorder, stabilized (i.e., not worsening) state of a disorder, delay or slowing of progression of a disorder, amelioration or palliation of the state of a disorder, remission (whether partial or total), whether detectable or undetectable, or combinations thereof. "Treatment" can also mean prolonging survival as compared to expected survival if not receiving treatment.

As used herein, the terms "therapeutic treatment" or "therapy" and the like, refer to treatments wherein the object is to bring a subjects body or an element thereof from an undesired physiological change or disorder to a desired state, such as a less severe or unpleasant state (e.g., amelioration or palliation), or back to its normal, healthy state (e.g., restoring the health, the physical integrity and the physical well-being of a subject), to keep it at said undesired physiological change or disorder (e.g., stabilization, or not worsening), or to prevent or slow down progression to a more severe or worse state compared to said undesired physiological change or disorder.

As used herein the terms "prevention", "preventive treatment" or "prophylactic treatment" and the like encompass preventing the onset of a disease or disorder, including reducing the severity of a disease or disorder or symptoms associated therewith prior to affliction with said disease or disorder. "Preventing" also encompasses preventing the recurrence or relapse-prevention of a disease or disorder for instance after a period of improvement.

A 'therapeutic amount' or 'therapeutically effective amount' as used herein refers to the amount of an active compound or pharmaceutical agent (e.g., a cell-based product) effective to treat a disease or disorder in a subject, i.e., to obtain a desired local or systemic effect. The term thus refers to the quantity of the cells, the compound or the agent that elicits the biological or medicinal response in a tissue, system, animal, or human that is being sought by a researcher, veterinarian, medical doctor or other clinician. Such amount will typically depend on the specific cell type, the compound or the agent and the severity of the disease, but can be decided by the skilled person, possibly through routine experimentation. The term "prophylactically effective amount" refers to an amount of cells, an active compound or pharmaceutical agent (e.g., a cell-based product) that inhibits or delays in a subject the onset of a disorder as being sought by a researcher, veterinarian, medical doctor or other clinician.

As used herein and unless otherwise stated, the term "periosteum derived cells" means any cell type that is isolated from the periosteum well known to a person skilled in the art.

As used herein and unless otherwise stated, the term "bone disorders" or "bone diseases" means any medical condition that affects the bone, examples of such bone disorders include but are not limited to bone diseases such as osteoporosis, Paget's disease, congenital pseudoarthrosis, osteoarthritis, osteosarcoma, diabetes, osteopetrosis, brittle bone disease, McCune-Albright Syndrome and Neurofibromatosis and also include bone injuries such as bone fractures, delayed union fractures and non-healing bone disorders and bone injuries resulting from trauma, infections and prosthesis revision.

As used herein and unless otherwise stated, the term "non-healing bone defect" or "non-healing bone disorder" or "nonunion bone defects" means permanent failing of healing of a structural defect of the bone leading to loss of integrity. Large non-healing bone defects can also be caused by other situations such as traumatic bone defects, as a result of infection, irradiation, prosthetic revision or in compromised patients such as diabetes, ostepoporosis and vascular disease; and smokers. Examples of such non-union bone defects include but are not limited to atrophic, hypertrophic fractures and large bone defects as known to a person skilled in the art.

"Micro aggregate" in the context of the present invention refers to a cluster of cells, originating from a suspension of between 25 and 50 000 cells, wherein the cells are in contact with each other. Such aggregates differ from cells which are distributed in a viscous or solid medium or in a scaffold. Such aggregates also differ from pellets of cells obtained by centrifugation of cells.

Micro aggregates which have been cultured according to the methods of the invention and have acquired a pre-hypertrophic phenotype as determined by expression markers, morphology or behaviour upon implantation are referred to as "micro-tissue".

"Pre-hypertrophic phenotype" in the context of the present invention refers to a cellular state of transient chondrocytes typically leading to mineralization and bone formation upon implantation. Exemplary gene markers for this phenotype are collagen type X (COL X), Indian hedgehog (IHH), alkaline phosphatase (ALP) and (bone sialoprotein) BSP. Pre-hypertrophic chondrocytes acquire a round morphology as compared to stem and progenitor cells.

When a plurality of microtissues is pooled these spontaneously fuse in the absence of a scaffold of defined 3D structure, into larger constructs, referred to as "fused microtissues". Fused microtisssues are thus clusters of clusters, and differ from micromasses which are derived from a 3D grown cell suspension of between 200,000-500,000 cells, and differ from a plurality of microtissues which are distributed in a viscous or solid medium or in a scaffold. The size of fused microtissues depends on the number and size of the individual constituent microaggregates and is determined by the size of the bone defect to be treated. As an alternative to "Fused microtissues", the term "macrotissue can be used The present invention relates to in vitro methods for producing a cellular composition with in vivo bone forming potential. In general the method comprises the steps of:
- culturing periosteum derived cells into micro-aggregates of a desired size,
- further cultivating the micro aggregates until the cells in the micro-aggregate obtain the phenotype of pre-hypertrophic cells forming micro tissues,
- fusing said cultured micro-tissues in the absence of a scaffold into a larger aggregate (fused microtissue).

Periosteum derived cells are obtained by taking a biopsy and subsequent mechanical and/or enzymatic treatment. Such isolation is described for example in Roberts et al. (2011) *Biomaterials*. 32, 4393-4405. Freshly isolated, expanded or passaged cells can form aggregates as explained for example in Bolander et al. 2017 wherein an appropriate number of cells is distributed over a plurality of small wells.

The aggregates are further cultivated to obtain a microtissue with a pre-hypertrophic phenotype. Methods and markers to detect such phenotype are disclosed and discussed in the examples section.

To obtain such phenotype the microaggregates are cultured in a serum free medium comprising at least one BMP. Various embodiments of such media are herewith disclosed. The at least one BMP may be at least one selected from the group consisting BMP2, BMP4, BMP6, BMP7, BMP9, or any combination thereof, such as BMP2, BMP6 or a combination of BMP-2 and BMP-6.

The concentration of the at least one BMP is between about 0.1 to 1000 ng/ml.

In a specific embodiments the at least one BMP is a combination of BMP-2 and BMP-6, wherein typically the concentration of BMP-2 is between about 10 to 1000 ng/ml and the concentration of BMP-6 is between about 0.1 to 10 ng/ml, and more specifically the concentration of BMP-2 is about 100 ng/ml and the concentration of BMP-6 is about 1 ng/ml.

In other embodiments, the further comprises at least one growth factor selected from the group consisting of TGF-beta1, FGF2, GDF5 or any combination thereof, typically in concentration from about 0.01 ng/ml to about 1000 ng/ml per growth factor, more specifically from about 0.01 ng/ml to about 100 ng/ml, and even more specifically the concentration of TGFbeta1 is about 10 ng/ml, the concentration of FGF2 is about 0.2 ng/ml, and the concentration of GDF5 is about 100 ng/ml.

In a specific embodiment the medium comprises about 10 ng/ml TGFbeta1, about 0.2 ng/ml FGF2, about 100 ng/ml GDF5, about 100 ng/ml BMP2, and about 1 ng/ml BMP6. In another specific embodiment the medium comprises: 1 to 100 ng/ml TGF beta 1, 0.05 to 10 ng/ml FGF2, 1 to 250 ng/ml BMP2, 0.25 to 2.5 ng/ml BMP6 and 1 to 250 ng/ml GDF5.

Media for use in the methods of the present invention may further comprise Dexamethasone, Rho-kinase inhibitor and Ascorbic Acid, typically in concentrations of about 10 to 1000 nM Dexamethasone, about 2 µM to about 200 µM Rho-kinase inhibitor, and about 10 to 1000 µM Ascorbic Acid, more typically about 100 nM Dexamethasone said about 20 µM Rho-kinase inhibitor about 100 µM Ascorbic Acid.

An example of such said Rho-kinase inhibitor is Y27632.

In a specific embodiment of the present invention, said serum free medium contains LG-DMEM, which further contains the following compounds:
- antibiotic-antimycotic (100 units/mL penicillin, 100 mg/mL streptomycin and 0.25 mg/mL amphotericin B), preferably at a concentration of about 1%
- ascorbate-2 phosphate, preferably at a concentration of about 100 µM
- dexamethasone, preferably at a concentration of about 100 nM
- proline, preferably at a concentration of about 40 µg/mL
- ITS+ Premix Universal Culture Supplement (including 6.25 µg/mL insulin, 6.25 µg/mL transferrin, 6.25 µg/mL selenious acid 1.25 µg/mL bovine serum albumin (BSA), and 5.35 µg/mL linoleic acid), preferably at a concentration of about 1%.

In specific embodiments of the present invention, said serum free medium as described hereinabove is used in all steps of the methods of this invention. In other specific embodiments of the present invention, said serum free medium as described hereinabove is used in all steps of the methods of this invention.

Microaggregates are cultivated until a pre-hypertrophic phenotype is obtained, which may range from at least 3, 7, 10 up to 14, 21, 28, 56 days. Typically the microaggregates are cultivated from 14 to 28 days. Microaggregates are made as disclosed for example in Moreira Teixeira (2012) or Bolander (2017) by spreading cell suspension on a carrier with microwells (eg in agarose), whereby the amount of cells is adjusted to obtain a concentration of cells/microwell ranging from 50, 100, 150, 200, 250, 500 up to 1000, 2500, 5000, 50 000 upon seeding. Marker analysis, morphology, and eventual ectopic implantation allows the person skilled in the art to determine the optimal cultivation conditions which may be influenced by the origin of the cells, the medium and the recipients.

The cultivated microaggregates differentiated into desired phenotype (also referred to as microtissues) are assembled into larger aggregates by spontaneous fusion (also referred to as fused microtissues). As explained in the examples the microtissues, which are already differentiated to a certain extent as can be appreciated by the presence of pre-hypertrophic markers, spontaneously fuse into larger aggregates. The fusion is typically performed in the same medium that was used for the cultivation, but can be equally performed in any other serum free medium [comprising at least one BMP].

The number of microtissues needed for fusion into a fused microtissue of a certain size depends on the number of cells used for the preparation of microaggregates and the subsequent cultivation time. This number can range from as low as 300, 500, 750, 1000 up to 3000, 6000, 10.000, 25.000, 50.000 or more.

The desired size of a fused microtissue depends on the size of the bone lesion to be repaired, and can range from 3 to 100 mm. Although the methods of the present invention are aimed to heal a bone lesion with a single fused microtissue, the shape or the size of the bone lesion may require the use of a plurality of fused microtissues for the healing of a bone lesion. The shape of final product can be modulated based on the configuration of the mold.

Another aspect of the present invention relates to a cellular composition of fused microtissues with in vivo bone forming potential produced by any of the methods of the present invention.

These cellular compositions, further comprising a biocompatible carrier. The fused microtissue may be collected from the medium and implanted as such. In alternative embodiments, a fused microtissue is formulated in biocompatible carrier to facilitate manipulation, storage or transport of the fused microtissue prior to implantation.

Such biocompatible carrier may comprises collagen, calcium phosphate, carboxymethyl cellulose, hydrogel or combinations thereof.

Yet another aspect of the present invention relates to a pharmaceutical composition comprising: the cellular composition according to the present invention and a pharmaceutically acceptable carrier, excipient or solution.

One embodiment of the present invention relates the cellular composition of the present invention for use as a medicine.

Another embodiment of the present invention relates to the pharmaceutical composition, comprising the cellular composition of the present invention, for use as a medicine. More specific embodiments of the present invention relate to the cellular composition or the pharmaceutical composition of the present invention for use as a medicine for the treatment of a subject or animal having a bone disorder. In a more specific embodiment thereof, said bone a bone fracture, a non-healing bone defect, an osteochondral defect or a metabolic bone disease.

Typically said bone disorder is a non-healing bone defect. A specific embodiment of the present invention relates to the cellular composition or the pharmaceutical composition of the present invention for use as a medicine for the treatment of a subject or animal having a non-healing bone defect, more specifically said subject is a mammal and even more specifically said mammal is a human patient. For such bone defects, the preferred cellular composition of the present invention is the one that is generated by the method of the present invention, comprising all steps from the generation of micro-aggregates up to, and including the fusion of the microtissues into fused microtissues.

Another aspect of the present invention relates to method of treatment of a bone disorder in an animal, comprising the administration to said animal of the cellular composition or the pharmaceutical composition of the present invention.

In specific embodiments of the present invention said animal is a mammal. In more specific embodiments of the present invention said animal is a human patient. Alternatively, the present invention concerns the use of the cellular composition produced according to any one of the methods of this invention or a pharmaceutical composition according to the present invention for use in medicine, more particularly for use in the treatment of a subject with a bone disorder. A more particular embodiment thereof relates to the treatment of a subject with a non-healing bone defect, more particularly said subject is a human patient.

In certain preferred embodiments, the subject, patient or animal is a human, more particularly a human with a bone defect, such as a non-healing bone defect.

One embodiment of the present invention concerns a method of treatment comprising administering a therapeutically effective amount of the cells or the cellular composition produced according to any one of the methods of this invention, to a subject with a bone disorder, said bone disorder includes a bone fracture. A specific embodiment of the present invention relates to said method of treatment or the use of the cellular composition to treat a subject, preferably a human, with a bone disorder such as a non-healing bone defect.

Apart from applications in human treatments, the methods of the present invention are equally applicable for veterinary applications, such as bone repair in racing horses and dogs.

Unless defined otherwise, all technical and scientific terms used herein have the same meaning as commonly understood by one of ordinary skill in the art in the field of the invention. Any methods and materials similar or equivalent to those described herein can also be used in the practice of the present invention, but the preferred methods and products are described herein.

EXAMPLES

Having provided a general disclosure, the following examples help to illustrate the general disclosure. These specific examples are included merely to illustrate certain aspects and embodiments of the disclosure, and they are not intended to be limiting in any respect. Certain general principles described in the examples, however, may be generally applicable to other aspects or embodiments of the disclosure.

Figure 1:
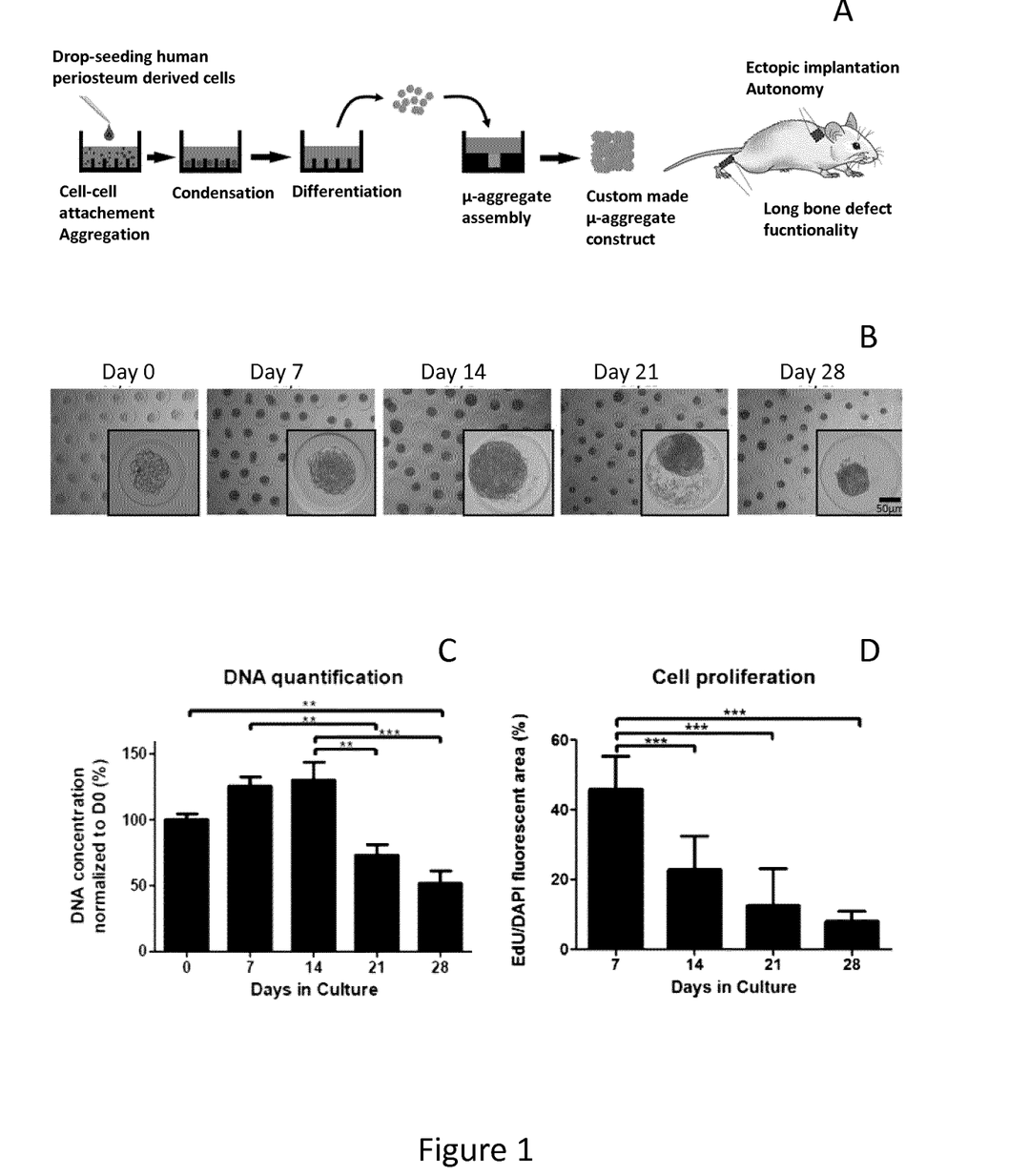

Example 1: Long-Term Culture of µ-Aggregates Follow Early Patterns of Endochondral Ossification In vivo endochondral ossification is initiated with cell aggregation and condensation, followed by chondrocyte differentiation and formation of a cartilage intermediate that is subsequently replaced by bone tissue (Mackie et al.). Here, the process of cell aggregation, condensation and differentiation of hPDCs was studied over a period of 4 weeks. The initial self-aggregation step comprised of two steps. Initially, over a course of 5 hours, hPDCs self-assembled to form a 2D+ stack of cells. Subsequently, a spheroid shape was attained (FIG. 1ab). Filamentous-actin (F-actin) staining indicated cytoskeleton reorganization during the first week as well as compaction of aggregates with more confined actin cortical network over time and finally of its thinning.

3D visualization of cell nuclei showed cell reorganization during the first week where after the cell density decreases and apoptotic cells were visible. Furthermore, DNA quantification demonstrated a stable amount of cells during the two first weeks followed by a 44% decrease after three weeks (n=6, FIG. 1c). The majority of cells in the µ-aggregates were viable however an increase of dead cells was observed during the after a four week culture period. Edu staining revealed a high amount of proliferating cells (46%) during the first weeks which decreased and was almost absent after four weeks in culture (n=8, FIG. 1d). This decrease in proliferation pattern is also seen during in vivo endochondral ossification [Mackie et al. (2011) *J. Endocrinol.* 211, 109-121] indicating differentiation of the µ-aggregate cells similar to the pattern as observed during naturel bone formation.

Figure 2:
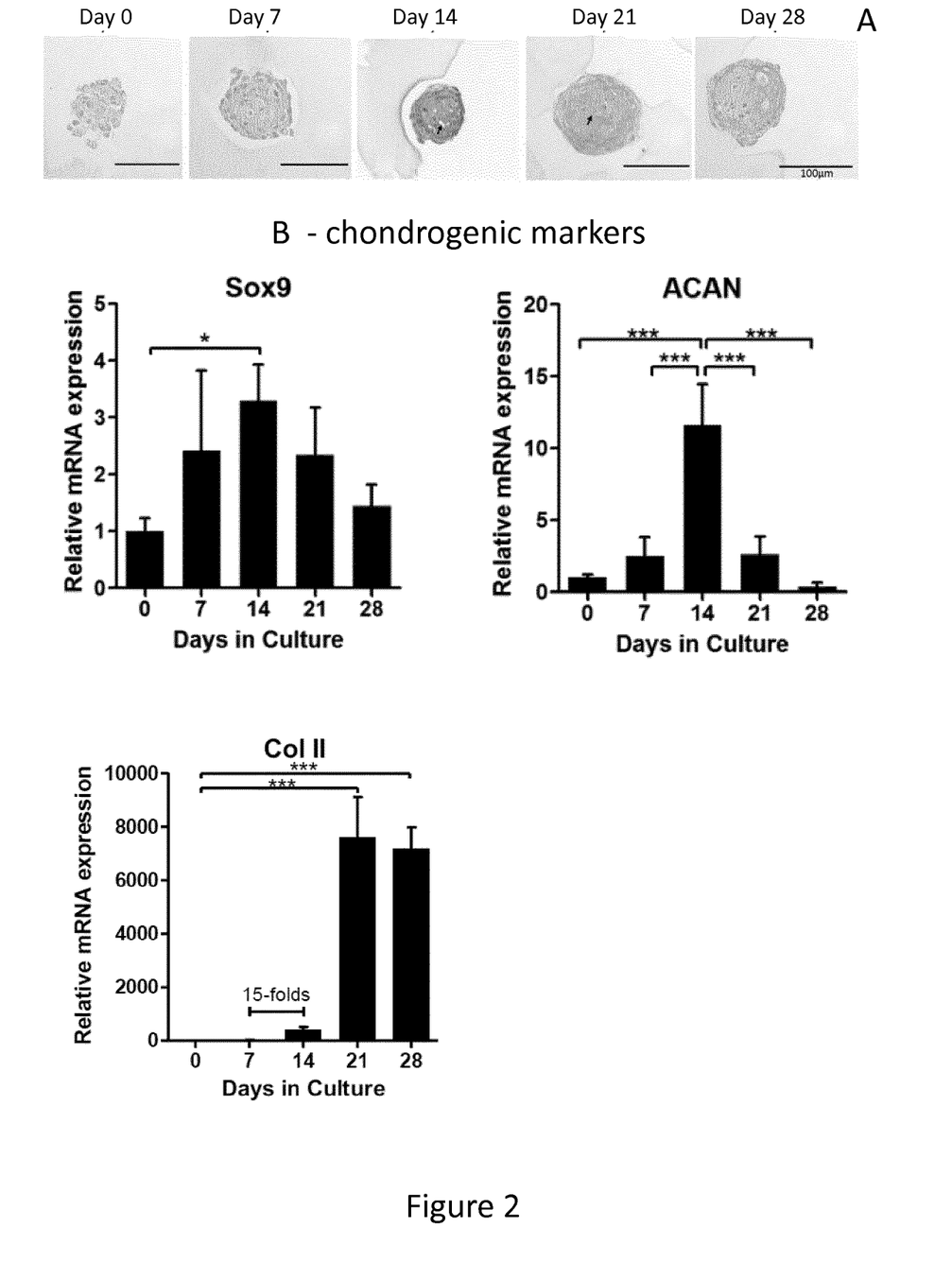
FIG. 2. μ-aggregates mature towards hypertrophic microtissues able to mineralize in vivo. (a) matrix comprising individual microtissues in ectopically implanted in mice. Quantification of mRNA transcript of (b) chondrogenic, pre-hypertrophic, (c) hypertrophic and (d) mineralization related markers. (e) Schematic of individual microtissue implantation. (f) 3D rendering of NanoCT images after 4 weeks in vivo implantation.

Example 2: µ-Aggregates Mature Towards Hypertrophic-Like Microtissues Able to Form µ-Bone Organoids In Vivo Alcian Blue staining, specific for glycosaminoglycan, confirmed an increasing deposition of cartilage-like ECM within the µ-aggregates until day 14, whereafter the Alcian blue staining remains similar after 21 and 28 days (FIG. 2a).

GAG content per DNA increased during culture time and pre-hypertrophic like cells were visible after three weeks in culture.

To further define the differentiation stage of μ-aggregates towards microtissues, gene expression of relevant markers was analysed (n=4). Early chondrogenic gene markers (SOX9 and ACAN) had a 3 and 10-fold peak up-regulated respectively after 14 days in culture while the chondrogenic marker COL II was $10^4$-fold up-regulated after 21 days in culture retaining similar levels of expression also after 28 days (FIG. 2b). The pre-hypertrophic marker RUNX2 was 10-fold up-regulated the first 14 days where after a down-regulation was detected (FIG. 2c). Down-regulation of RUNX2 was exchanged by an up-regulation of hypertrophic markers, 800-fold up-regulation of COL X, 35-fold up-regulation of IHH day 21 and 20-fold up-regulation of ALP day 14 (FIG. 2d). BSP, linked to the transition from cartilage to bone during endochondral ossification [Holm et al. (2015) Bone. 71, 145-154], was 900-fold up-regulated after 21 days in culture.

The methods of the present invention accordingly foresee an optional quality control step wherein the expression levels of one of more of COL X, IHH, ALP and BSP are measured in the cultivated aggregates, or in the fused microtissues and compared with newly formed aggregates for a 50, 100 or 500 fold upregulation of CoIX, or a 5, 10 or 20 fold upregulation of Ihh, or for a 10 or 20 fold upregulation of ALP, or for a 10, 100 or 1000 fold upregulation of BSP. Cultivated aggregates or fused microtissues with one or more of the above mentioned expression levels are preferred for use in bone repair.

Based on the presence of hypertrophic cells (FIG. 2a) and the up-regulation of hypertrophic gene markers (FIG. 2d), day 21 microtissues were chosen to be implanted subcutaneously to evaluate their capacity to mature in vivo. Implantation of whole agarose micro-well platforms with a diameter of 5 mm was carried out in immunodeficient mice (FIG. 2f) ensuring that microtissues would remain entrapped in their μ-wells and would not assemble by fusion into larger fused microtissues. After 4 weeks ectopic implantation (n=3), nano-CT scans demonstrated the formation of mineralized spheres (FIG. 2g) with a volume of $6.0 \pm 1.8 \times 10^5$ μm$^3$ (n=11). Histologic sections further showed the presence of osteoblasts in bone matrix surrounding a compartment with blood vessels and osteoclasts. These data demonstrated the formation of μ-bone constructs with a diameter of $222 \pm 23$ μm (n=11), confirming the fact that these implants as single modules, autonomously could undergo endochondral ossification. As a control, implants of microaggregates, fused after 7 days cultivation failed to form bone upon implantation.

Example 3: Microtissues Fuse into Large Homogenous Constructs

Figure 3:
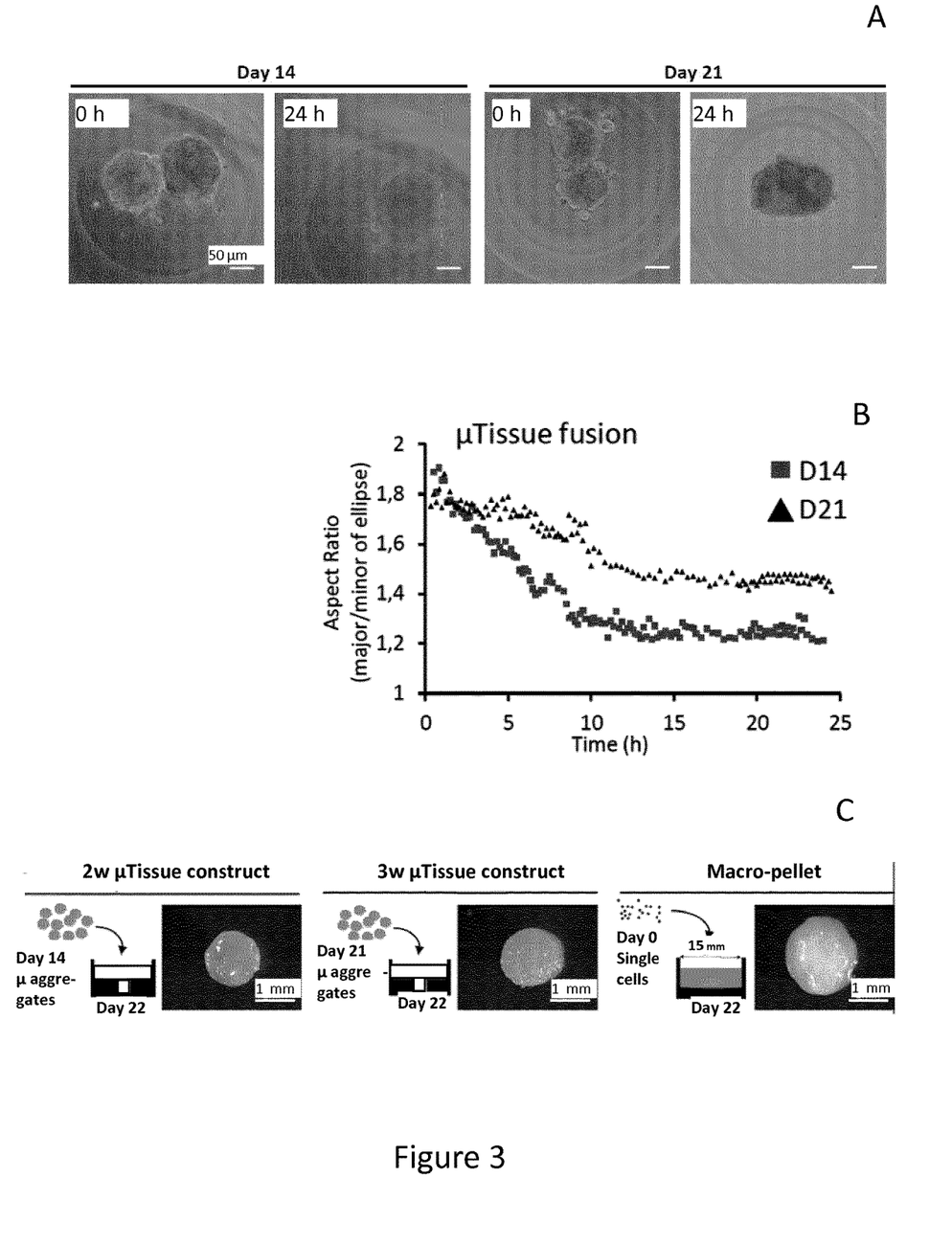
FIG. 3. fusion of microtissues into large constructs. (a) 24 hours fusion of two microtissues with 14 and 21 days of maturation. (b) Quantification of the fusion according to the aspect ratio: major divided by minor diameter of a fitted ellipse. (c) Schematic drawing and representative photographs of the constructs 2 w fused microtissue, 3 w fused microtissue construct and a macro pellet.

In order to demonstrate that the above mentioned microtissues were able to form larger tissues we initially studied the fusion process of two microtissues. Despite long-term culture of more than 2 weeks as separate microtissues, with already a substantial amount of secreted ECM, they nevertheless surprisingly spontaneously fused within 24 hrs (FIG. 3a). Next, multiple microtissues (~3000) were fused in in-house developed 3 mm Ø agarose wells. microtissues cultivated for 14 days (2 w) and 21 days (3 w) were chosen for further analysis based on chondrogenic (SOX9, ACAN, COL II) and hypertrophic (COL X, IHH, ALP) gene markers (FIG. 2b-d), respectively as well as cell morphology (FIG. 2a). Both 2 w and 3 w microtissues fused into larger constructs that could be handled and transported (FIG. 3b-c), however single microtissue structures were still discernible after fusion of microtissue constructs into larger aggregates of fused microtissues. As control to these fused structures, a macro-pellet formed with the same amount of cells and cultured for 3 weeks in the same media formulation was introduced (FIG. 3c).

Alcian Blue staining of fused microtissues demonstrated a more compact tissue for a fused microtissue obtained with 2 w microtissue (FIG. 3b) compared to a fused microtissue obtained with 3 w microtissue (FIG. 3c), albeit both constructs had positive staining throughout. In contrast, the macro-pellet did only contain Alcian Blue staining at the periphery (FIG. 3d). Collagen II immunostaining corresponded to the Alcian Blue staining seen in macro-pellets and certain parts of the fused microtissues obtained with 3 w microtissue construct were collagen II positive. These results demonstrated the formation of microtissue constructs containing more homogenously distributed glycosaminoglycan rich ECM compared to macro-pellets.

Example 4: Microtissue Constructs Mature into Bone Like Structures In Vivo and Heal Critical Size Bone Defect Next, the fused microtissues obtained with 2 w and 3 w microtissue constructs as well as the macro-pellets were implanted ectopically in immunodeficient mice to validate their capacity to mature into bone after 4 and 8 weeks in vivo. Mineralization was detected with nano-CT in all three conditions after 4 weeks implantation with the fused microtissues obtained with 2 w microtissue constructs containing the highest and macro-pellets the lowest amount of mineralized tissue. No significant difference was seen after 8 weeks, nevertheless a non-mineralized core was detected in the macro-pellet constructs. Furthermore, the fused microtissue obtained with 3 w microtissue constructs and macro-pellets contained a mineralized cortex while the mineralized tissue in the fused microtissue obtained with 2 w microtissue constructs appeared porous.

Figure 4:
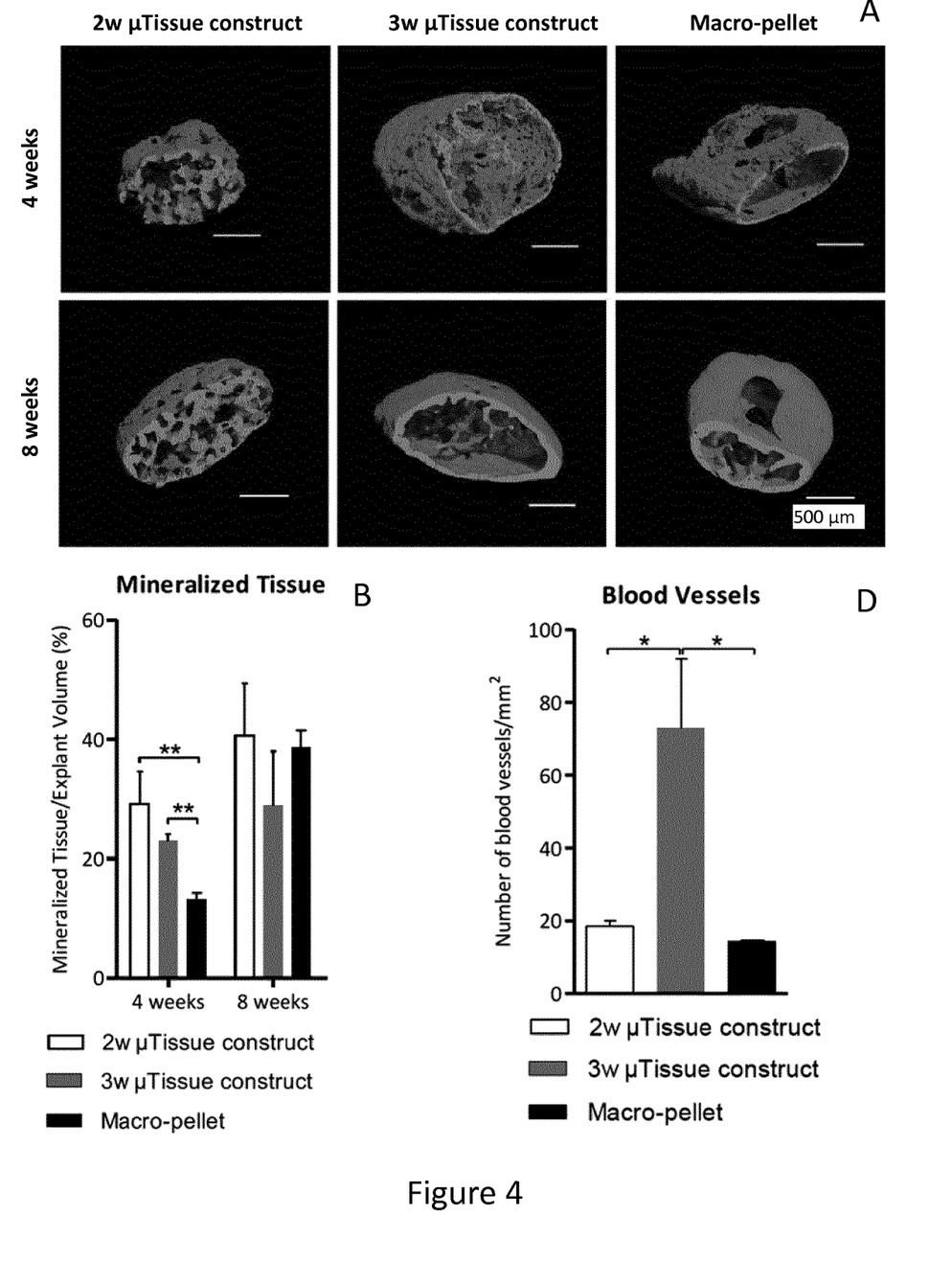
FIG. 4. Presence of mineralization and blood vessels after ectopic implantation. (a) 3D visualization of mineralized tissue after 4 and 8 weeks ectopic implantation with (b) quantification normalized to the total construct volume. (c) C31 immunostaining for blood vessel visualization after 8 weeks ectopic implantation. (d) Quantification of CD31 staining on constructs after 8 weeks ectopic implantation.
Figure 5:
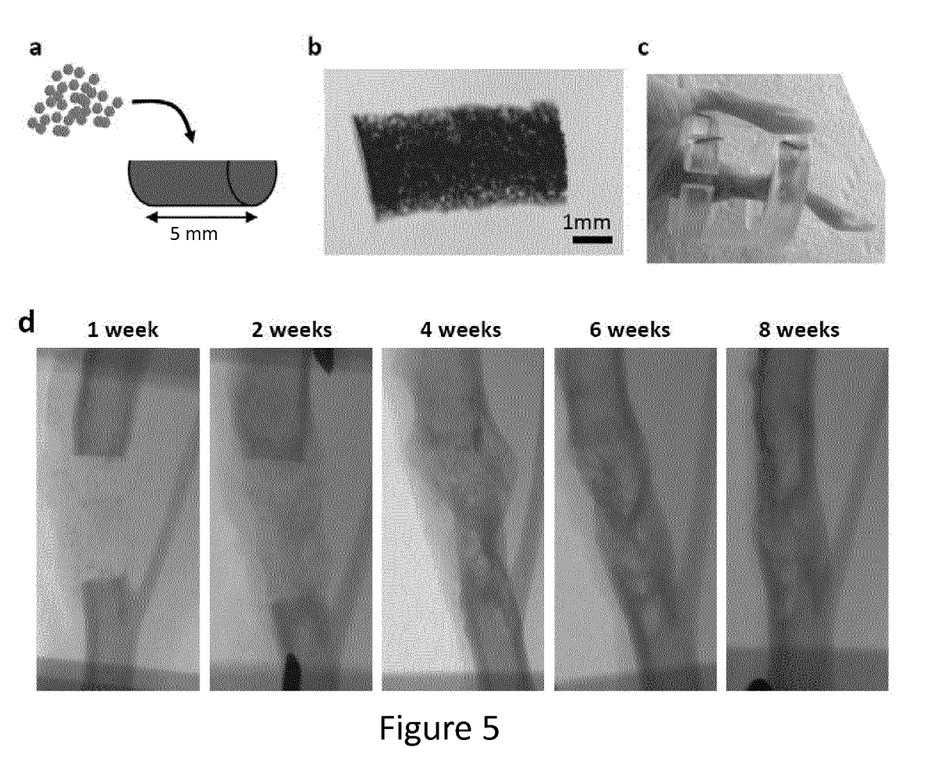

After 4 weeks implantation, Safranin O staining on histology sections revealed that the fused microtissue obtained with 3 w microtissue constructs contained bone, bone marrow as well as remodelling cartilage indicating the occurrence of endochondral ossification (FIG. 4b). Bone marrow compartments were not detected in the fused microtissue obtained with 2 w microtissue constructs (FIG. 4a) nor macro-pellets (FIG. 4c) both in contrast to the 3 w microtissue constructs; areas of fibrotic tissue were detected in both the fused microtissue obtained with 2 w microtissue constructs and macro-pellets. Mature bone was present in all conditions after 8 weeks implantation but the fused microtissue obtained with the 2 w microtissue constructs and macro-pellets still contained domains of fibrotic tissue which were absent in the fused microtissue obtained with the 3 w microtissue constructs. Largest bone marrow compartments were found in the fused microtissue obtained with the 3 w microtissue constructs which also contained 4-fold more blood vessels (FIG. 4d). Furthermore, hOCN staining demonstrated the contribution of implanted cells to bone formation. Taken together these results showed that the fused microtissue obtained with 3 w single microtissues fused in vitro to further develop into large bone organoids in vivo lacking fibrous tissue. Bridging of critical sized long bone defect Based on the ectopic implantation results, the fused microtissue obtained with 3 w microtissues were selected for the formation of a large constructs for orthotopic implantation in a murine, critically sized long bone defect. An agarose mould based on the dimensions of the critical size defect (FIG. 5a), as obtained from nanoCT scans, was fabricated. Next, 6 000 microtissues were seeded into the mould and fused during 24 hrs resulting in a 5 mm long construct that was fitted into the tibia defects of immunodeficient mice (n=4). Mineralization was detected after 2 weeks and bridging of the defects was evident after 4 weeks (n=3) (FIG. 5c). Furthermore, a cross-section of nano-CT 3D rendering demonstrated the presence of cortical bone in the defect with a non-mineralized compartment in the centre (FIG. 5f) suggesting a defined bone marrow cavity (FIG. 5g). Masson's Trichrome staining confirmed the presence of mature bone and hOCN staining revealed the contribution of donor cells to the bone formation process. In conclusion, the assembly of multiple pre-hypertrophic-like microtissues into an easy-to-handle scaffold-free implant resulted in full bridging of a critically sized long bone defect by the formation of cortical-like bone tissue, containing bone marrow with the absence of fibrous tissue.

Materials & Methods

Cell Expansion

A pool of human periosteum derived cells (hPDCs) was created of hPDCs isolated from periosteal biopsies of four different donors (n=4; two female and two male donors; age 28.8 years±12.3) as previously described (Eyckmans et al.). The hPDC pool was expanded until passage 8-10 (5700 cells/cm$^2$) at 37° C., 5% $CO_2$ and 95% humidity in Dulbecco's modified Eagle's medium (DMEM, Life Technologies, UK) with 10% fetal bovine serum (HyClone FBS, Thermo Scientific, USA), 1% antibiotic-antimycotic (100 units/mL penicillin, 100 mg/mL streptomycin and 0.25 mg/mL amphotericin B) and 1 mM sodium pyruvate (Life Technologies, UK). Medium was changed every 2-3 days and cells were harvested with TrypLE™ Express (Life Technologies, UK) at a confluence of 80%-90%. TrypLE™ Express was used for all passaging and harvesting steps during cell handling. The ethical committee for Human Medical Research (Katholieke Universiteit Leuven) approved all procedures, and patients' informed consent forms were obtained.

Formation of μ-Aggregates

A polydimethylsiloxaan (PDMS) μ-aggregate mould described in Moreira Teixeira et al. with slight modifications was used for formation of μ-aggregates. Micro-wells had a diameter of 200 μm and depth of 170 μm. Micro-well inserts were made by preparing 3% w/v agarose (Invitrogen, Belgium) that was poured onto the PDMS mould. The agarose was let to solidify where after micro-well inserts with an approximate area of 1.9 cm$^2$ were punched out, placed in 24-well plates and sterilized under UV. Each well insert contains approximately 2000 micro-wells. hPDCs were harvested and seeded with a concentration of 250 000 cells/mL to obtain ~250 cells/aggregate after self-aggregation. μ-aggregates were differentiated into microtissues in a serum-free chemically defined chondrogenic medium containing LG-DMEM (Gibco) supplemented with 1% antibiotic-antimycotic (100 units/mL penicillin, 100 mg/mL streptomycin and 0.25 mg/mL amphotericin B), 100 μM ascorbate-2 phosphate, 100 nM dexamethasone, 40 μg/mL proline, 20 μM of Rho-kinase inhibitor Y276323 (Axon Medchem), ITS+ Premix Universal Culture Supplement (Corning) (including 6.25 μg/mL insulin, 6.25 μg/mL transferrin, 6.25 μg/mL selenious acid, 1.25 μg/mL bovine serum albumin (BSA), and 5.35 μg/mL linoleic acid), 100 ng/mL BMP-2 (INDUCTOS®), 100 ng/mL GDF5 (PeproTech), 10 ng/mL TGFβ1 (PeproTech), 1 ng/mL BMP-6 (PeproTech) and 0.2 ng/mL FGF-2 (R&D systems) (Freitas Mendes et al.). Half of the media volume was changed every 3-4 days.

Viability Assay

Cell viability in micro-aggregates was visualized qualitatively with LIVE/DEAD® Viability/Cytotoxicity Kit for mammalian cells by following the manufacturer's protocol (Invitrogen, USA). Briefly, micro-aggregates were rinsed with PBS, where after they were incubated in 2 μM Calcein AM and 4 μM Ethidium homodimer-1 for 30 min at 37° C., 5% $CO_2$ and 95% humidity. Stained micro-aggregates were visualized with confocal microscope ZEISS LSM 510 META (Cell imaging core facility of KU Leuven) with 4 μm thick slices.

Cell Proliferation Assay

Cell proliferation during micro-aggregate differentiation was measured with Click-iT® EdU (5-ethynyl-2'-deoxyuridine) Imaging Kit (Life Technologies, USA) according to the manufacturer's protocol. Briefly, 10 μM EdU was added to the micro-aggregates during 4 days for each time point. Samples were fixed in 4% Paraformaldehyde (PFA) and then visualized with Leica M165 FC microscope (Microsystems, Belgium). The percentage of EdU/Hoechst (proliferating cell/all cells) stained area was quantified using ImageJ software (Rasband) for 10-15 micro-aggregates per time point.

Cytoskeleton and Nuclei Visualization

Cell and filamentous actin (F-actin) distribution within micro-aggregates was visualized by staining during 1 hour at room temperature with 2.5 μg/ml 4',6-diamidino-2-phenylindole (DAPI) (Invitrogen) and 0.8 U/mL Alexa Fluor 488® phalloidin (Invitrogen), respectively. Stained micro-aggregates were imaged with confocal microscope ZEISS LSM 510 META (Cell imaging core facility of KU Leuven), with fpm thick slices.

DNA Quantification, Total RNA Extraction and Quantitative Reverse Transcription-Polymerase Chain Reaction Analysis Quantitative real-time polymerase chain reaction (qRT-PCR) was used to quantify mRNA of markers relevant for endochondral ossification. Micro-aggregates were washed in PBS followed by cell lysis in 350 μl RLT lysis buffer (Qiagen, Germany) and 3.5 μl β-mercaptoethanol (Sigma Aldrich, Germany), vortexed and stored at −80° C.

DNA assay kit QuantitT™ dsDNA HS kit (Invitrogen) was used to quantify the DNA content for each condition. Cell lysate was spun down and the DNA assay was performed according to the manufacturer's protocol. Remaining samples were stored at −80° C. for mRNA quantification.

RNeasy Mini Kit (Qiagen) was used to isolate the total amount of RNA from lysed cells that were thawed from −80° C. After RNA extraction, the RNA concentration was quantified with NanoDrop 2000 (Thermo Scientific) and sample purity was evaluated at A260/A280 (protein purity; ~2.0+) and A260/A230 (salt purity; 2.0-2.2). RevertAid H Minus First Strand cDNA Synthesis Kit (Thermo Scientific, USA) was used for reverse transcription; 500 ng RNA was mixed with 1 μg oligo$^{(dT18)}$ for each reaction (5 minutes at 65° C.). The reaction mixture (4 μl 5× reaction buffer, 1 μl ribolock ribonuclease inhibitor, 2 μl dNTPmix (10 mM) and 1 μl RevertAid H Minus M-MuL VRT) was added to the samples and run in Applied Biosystems® Veriti® 96-Well Fast Thermal Cycler (60 minutes at 42° C. followed by 10 minutes at 70° C.). qRT-PCR was further performed from the cDNA with SYBR® Green (Life Technologies) and primers designed for the specific human markers in (Cycling: 95° C., 3 sec; 60° C., 20 sec). Three house-keeping genes were screened (hypoxanthine phosphoribosyltransferase 1 (HPRT1), beta actin and glyceraldehyde 3-phosphate dehydrogenase (GAPDH)) and GAPDH was found to be most stable. Relative differences in expression were calculated using the $2^{-\Delta\Delta Ct}$ method (Livak and Schmittgen).

Formation of Microtissue Constructs

Macro-wells with a diameter of 3 mm and depth of 2 mm (ectopic implantation) and length of 5 mm, width of 1 mm and depth of 2 mm (orthotopic implantation) were constructed with 3% w/v agarose (Invitrogen, Belgium) and sterilized under UV. microtissues were recuperated from their culture by gently pipetting up and down several times. Correct amount of microtissues were added (3 000 for ectopic and 6 000 for large bone defect implantation) to the macro-wells and incubated for 1 hours to sediment, where after chondrogenic media was added and constructs were incubated for additional 23 hours to fuse into microtissue constructs.

In Vivo Implantation of Microtissue Constructs

Subcutaneous implantation was used to validate the construct's autonomy to form cartilage and bone tissue. Bone and cartilage does not naturally form in this location and chondro- and osteo-inductive signals must therefore arise from the construct itself. When fused, the constructs were implanted subcutaneously in immune compromised mice (NMRI$^{nu/nu}$). Explants were taken 4 and 8 weeks after in vivo implantation and fixed in 4% PFA for subsequent nano-CT and histological analysis.

A large bone defect mouse model, described elsewhere (van Gastel et al.), was used to assess the impact of the environment and mechanical loading on the bone forming potential of the fused microtissues. Briefly, a custom-made Ilizarov fixator was fixed to the tibia using 27 G steel needles. The tibia was exposed and a 5 mm mid-diaphyseal segment was removed with a diamond saw. Custom made fused microtissue constructs (6 000 microtisses/construct, n=4) were placed into the defect and the skin was sutured to close the wound. An empty defect was used as control (n=4). Defects were monitored with in vivo μCT 1, 2, 4, 6 and 8 weeks after surgery. Animals were sacrificed after 8 weeks, the tibia was fixed in 4% PFA and analysed with ex vivo nanoCT and processed for histology.

Quantification of In Vivo Formation of Mineralized Tissue by nanoCT

Ex vivo nanoCT (Pheonix Nanotom M®, GE Measurement and Control Solutions) was used to quantify the amount of mineralized tissue in each explant. Explants were scanned with diamond target, mode 0, 500 ms exposure time, 1 frame average, 0 image skip, 2400 images and a 0.2 mm aluminium filter. Subcutaneous explants were scanned at a voltage of 60 kV and a current of 140 μA resulting in a voxel size of 2 μm. Large bone defect explants were scanned at a voltage of 60 kV and a current of 390 μA resulting in a voxel size of 5.6 μm as well as with 60 KV and 175 μA resulting in a voxel size of 2.5 μm. CTAn (Bruker micro-CT) was used for image processing and quantification of mineralized tissue.

Histochemical and Immunohistochemical Characterization

Retrieved subcutaneous explants were fixed in 4% PFA overnight and decalcified in ethylenediaminetetraacetic acid (EDTA)/PBS (pH 7.5) for 10 days at 4° C. Tibias were fixed in 2% PFA overnight and decalcified in EDTA/PBS (pH 7.5) for 3 weeks then dehydrated and embedded in paraffin. Ectopic samples were sectioned at 5 μm and tibias at 6 μm. Histolog3y was performed according to previously reported methods of hematoxylin-eosin, alcian blue and safranin O staining. Immunostaining.

Statistical Analysis

Statistical analysis was performed using one-way ANOVA and results were considered statistically different for p-values lower than 0.05 (*p<0.05, p<0.01, *p<0.001). All experiments were performed in triplicates, if nothing else is noted, and data are presented as mean+/− standard deviation.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. An in vitro method for producing a cellular composition with in vivo bone forming potential, the method comprising:
   generating micro-aggregates of between 25 and 50,000 periosteum derived cells;
   culturing the micro-aggregates for at least 10 days in a serum free medium comprising BMP2, in order to allow the micro-aggregates to differentiate into a micro-tissue with a pre-hypertrophic cartilage phenotype; and
   fusing, in the absence of a scaffold, at least 300 of the micro-tissues into a fused micro-tissue.

2. The method according to claim 1, wherein the micro-aggregates are cultured for between 14 to 28 days in the serum free medium comprising BMP2.

3. The method according to claim 1, wherein the micro-tissue with pre-hypertrophic cartilage phenotype expresses hypertrophic or mineralization related markers.

4. The method according to claim 1, wherein the serum free medium is free from FGF2 or comprises between 0.05 to 10 ng/ml FGF2.

5. The method according to claim 1, wherein micro-aggregates of between 25 and 5,000 periosteum derived cells are generated.

6. The method according to claim 1, wherein micro-aggregates of about 250 periosteum derived cells are generated.

7. The method according to claim 1, further comprising culturing the fused micro-tissue.

8. The method according to claim 1, further comprising formulating the fused micro-tissue into a biocompatible carrier.

9. The method according to claim 8, wherein the biocompatible carrier comprises collagen, fibrinogen, calcium phosphate, carboxy methyl cellulose, polyglycolic acid (PGA), Poly-lactic acid (PLA), poly-caprolactone (PCL), graphene, hydrogel or combinations thereof.

10. The method according to claim 1, wherein about 300 to 20×10⁶ micro-tissues are fused into the fused micro-tissue.

11. The method according to claim 1, wherein about 6000 micro-tissues are fused into the fused microtissue.

12. The method according claim 1, wherein the serum free medium comprises:
about 10 ng/ml TGFbeta1;
about 0.2 ng/ml FGF2;
about 100 ng/ml GDF5;
about 100 ng/ml BMP2; and
about 1 ng/ml BMP6.

13. The method according to claim 1, wherein the serum free medium comprises:
1 to 100 ng/ml TGF beta 1;
0.05 to 10 ng/ml FGF2;
1 to 250 ng/ml BMP2;
0.25 to 2.5 ng/ml BMP6; and
1 to 250 ng/ml GDF5.

14. The method according to claim 1, wherein the serum free medium comprises Dexamethasone, a Rho-kinase inhibitor and Ascorbic Acid.

15. The method according to claim 1, wherein the serum free medium comprises:
about 10 to 1000 nM Dexamethasone;
about 2 µM to about 200 µm Rho-kinase inhibitor; and
about 10 to 1000 µM Ascorbic Acid.

16. The method according to claim 1, wherein the serum free medium comprises:
about 100 nM Dexamethasone;
about 20 µM Rho-kinase inhibitor; and
about 100 µM Ascorbic Acid.

17. The method according to claim 14, wherein the Rho-kinase inhibitor is Y27632.

18. The method according to claim 1, wherein the serum free medium comprises:
a basal cell culture medium;
an antibiotic-antimycotic;
proline;
insulin;
transferrin;
selenious acid;
bovine serum albumin, and
linoleic acid.

19. A method of treating a bone disorder in an animal in need thereof, the method comprising administering a therapeutically effective amount of the cellular composition produced by the method of claim 1 to the animal.

20. The method according to claim 19, wherein the bone disorder is a bone fracture, a non-healing bone defect, an osteochondral defect, or a metabolic bone disease.

\* \* \* \* \*

UNITED STATES PATENT AND TRADEMARK OFFICE
CERTIFICATE OF CORRECTION

PATENT NO. : 11,278,645 B2
APPLICATION NO. : 16/617130
DATED : March 22, 2022
INVENTOR(S) : Frank Luyten et al.

It is certified that error appears in the above-identified patent and that said Letters Patent is hereby corrected as shown below:

In the Specification

In Column 4, Line(s) 17, delete "1000 μM" and insert --1000 nM--, therefor.

Signed and Sealed this
Twenty-fifth Day of October, 2022

*Katherine Kelly Vidal*

Katherine Kelly Vidal
*Director of the United States Patent and Trademark Office*